US012667476B2

(12) United States Patent　　　　(10) Patent No.:　US 12,667,476 B2
Klimmer　　　　　　　　　　　　　　(45) Date of Patent:　Jun. 30, 2026

(54) ADJUSTABLE ORTHOSIS JOINT FOR THE CONTROLLED MOVEMENT AND/OR FIXATION OF A HAND, AND ORTHOSIS HAVING AN ORTHOSIS JOINT OF THIS KIND

(71) Applicant: KIMEBO UG (HAFTUNGSBESCHRÄNKT), Munich (DE)

(72) Inventor: Uwe Klimmer, Munich (DE)

(73) Assignee: KIMEBO UG (HAFTUNGSBESCHRÄNKT), Munich (DE)

( * ) Notice: Subject to any disclaimer, the term of this patent is extended or adjusted under 35 U.S.C. 154(b) by 199 days.

(21) Appl. No.: 18/685,246

(22) PCT Filed: Aug. 23, 2022

(86) PCT No.: PCT/DE2022/100632
§ 371 (c)(1),
(2) Date: Feb. 21, 2024

(87) PCT Pub. No.: WO2023/025354
PCT Pub. Date: Mar. 2, 2023

(65) Prior Publication Data
US 2025/0120838 A1　　Apr. 17, 2025

(30) Foreign Application Priority Data
Aug. 23, 2021　(DE) ..................... 10 2021 121 819.5

(51) Int. Cl.
*A61F 5/01* 　　　(2006.01)

(52) U.S. Cl.
CPC ...... *A61F 5/013* (2013.01); *A61F 2005/0134* (2013.01); *A61F 2005/0167* (2013.01)

(58) Field of Classification Search
CPC .......... A61F 5/01; A61F 5/0118; A61F 5/013; A61F 5/0123; A61F 5/0125;
(Continued)

(56) References Cited

U.S. PATENT DOCUMENTS

| | | | |
|---|---|---|---|
| 7,081,102 B1 | 7/2006 | Koetter |
| 2004/0019306 A1 | 1/2004 | Brewer |

(Continued)

FOREIGN PATENT DOCUMENTS

| | | |
|---|---|---|
| CN | 210843695 | 6/2020 |
| DE | 102019130404 | 5/2021 |

(Continued)

*Primary Examiner* — Alireza Nia
*Assistant Examiner* — Gina Mccarthy
(74) *Attorney, Agent, or Firm* — JMB Davis Ben-David

(57) ABSTRACT

Described herein is an adjustable orthesis joint for the controlled movement and/or fixation of a hand of a patient and to an orthesis having such an orthesis joint, which is distinguished in that it includes at least one fastening element for pivotable fastening of a first pivot lever; at least one first, upper angle adjustment element, and at least one second, lower angle adjustment element; the first angle adjustment element and the second angle adjustment element each including at least one pivot limitation, which limit the extension and/or flexion movement of a first pivot lever in its range of movement.

16 Claims, 6 Drawing Sheets

(58) Field of Classification Search
CPC ................ A61F 5/0585; A61F 5/05858; A61F
5/05866; A61F 2005/0132; A61F
2005/0134; A61F 2005/0165; A61F
2005/0167; A61F 2005/0158; A61F
2005/0137; A61F 2005/0141; A61F
2005/0144; A61F 2005/0146; A61F
2005/0148; A61F 2005/0151; A41D
19/01582; A41D 19/01588; A61H 1/0285;
A61H 1/0288
See application file for complete search history.

(56)                     References Cited

U.S. PATENT DOCUMENTS

| | | |
|---|---|---|
| 2011/0282253 A1 | 11/2011 | Menon |
| 2018/0193179 A1* | 7/2018 | Baghaei Roodsari ....................... A61F 5/0102 |
| 2021/0145620 A1 | 5/2021 | Kumar |

FOREIGN PATENT DOCUMENTS

| | | |
|---|---|---|
| EP | 0546331 | 6/1993 |
| EP | 0832624 | 4/1998 |
| WO | 2021093919 | 5/2021 |

* cited by examiner

1

ADJUSTABLE ORTHOSIS JOINT FOR THE CONTROLLED MOVEMENT AND/OR FIXATION OF A HAND, AND ORTHOSIS HAVING AN ORTHOSIS JOINT OF THIS KIND

CROSS-REFERENCE TO RELATED APPLICATION

This is the U.S. National Stage of International Patent Application No. PCT/DE2022/100632 filed on Aug. 23, 2022, which claims priority to German Patent Application No. 10 2021 121 819.5 filed on Aug. 23, 2021.

The present invention relates to an adjustable orthesis joint for the controlled movement and/or fixation of a hand of a patient, comprising at least a first pivot lever for performing an extension and/or flexion movement of the hand and a second pivot lever, arranged pivotably on the first pivot lever, for performing an ulnar and/or radial deviation of the hand, as well as to an orthesis for the controlled movement and/or fixation of a hand, or of a hand and a forearm, of a patient, having such an orthesis joint.

In the scope of the rehabilitation process after a hand injury, the relevant hand or the forearm of the patient in many cases needs to be immobilized for some time. The immobilization is in this case usually carried out with hand/forearm ortheses that fixate the hand and forearm in a particular position and no longer allow any movement of said members after fixation has been carried out. An orthesis designed for fixation of the hand or forearm is disclosed, for example, in US 2021/014 56 20 A1. The rail described therein consists of at least two adjustable holding means, which can exert pressure onto the palmar or dorsal upper side of the forearm. By controlled alignment of said holding means with respect to one another and subsequent fixing in a desired position, the bone fragments of a forearm fracture can be stabilized in the scope of a fracture treatment. In this case, however, joints of the hand and/or of the forearm, which are entirely unaffected by the injury, are also necessarily immobilized. Depending on the length of time for which such an orthesis is worn, this may disadvantageously lead to so-called secondary stiffnesses of the joints not affected by the injury, the additional mobilization of which after the end of the healing process entails unnecessary costs because of an extended rehabilitation time and therefore longer unavailability of the patient for work. In the case of complex injuries to the hand or forearm, it may furthermore be desirable for individual joints which are more progressed in their healing process already to be moved in a controlled way while continuing to fixate joints that are still more greatly damaged. A "controlled movement" is in this context intended in particular to mean a movement performed while being restricted in terms of its movement angle. In physiotherapy and orthopedics, inter alia ortheses that hold members and enable the movement of a particular joint in a predefined angle range, so that the patient can perform the movement independently and safely, are often used for this purpose. The angle range may then be gradually extended depending on the state of training or the state of health of the patient, in order finally to recover the original movement radius.

Such range-of-motion (ROM) devices, in particular for knee ortheses, i.e. for the bending and straightening movement of the knee, are known from the prior art. For example, EP 0 546 331 A1 and EP 0 832 624 A2 disclose orthesis joints having an adjustable range of movement in relation to movement in a plane, which may preferably be used in a knee orthesis. Furthermore, US 7,081, 102 B1 discloses a carpal tunnel support having a joint, which allows a restricted radial and/or ulnar deviation of the hand of the user. A similar device for controlled deviation of the hand is described in CN 2 10 843 695 U.

The human hand joint, however, is distinguished by a more complex "multidimensional" range of movement, which may be described by a combination of an extension/flexion movement (bending and straightening movement in a plane perpendicular to the palm of the hand) and of an ulnar or radial deviation (waving movement in the plane of the palm of the hand). The orthesis joints and ROM devices known from the prior art, which are adjustable in their range of movement, cannot enable the control of such a multidimensional movement, or require a plurality of separate joints. By way of example, WO 2021/093 919 A2may be mentioned in this regard.

On the basis thereof, the object of the present invention is to provide an orthesis joint that is improved in comparison with the prior art, in particular for a hand orthesis, which makes it possible to control both an extension/flexion movement and an ulnar and/or radial deviation of the hand of a patient, while being constructed as compactly as possible but nevertheless being configured robustly.

This object is achieved by an adjustable orthesis joint having the features of independent patent claim 1 and by an orthesis having the features of the alternative independent patent claim 10.

The orthesis joint according to the invention is distinguished in comparison with orthesis joints of the prior art in that the orthesis joint comprises a fastening element for pivotable fastening of the first pivot lever; a first, upper angle adjustment element, which during use is arranged in relation to the back of a hand above the fastening element, rotatably about a rotation axis, on the fastening element; and a second, lower angle adjustment element, which during use is arranged in relation to the back of a hand below the fastening element, rotatably about the rotation axis, on the fastening element; the first angle adjustment element and the second angle adjustment element each comprising at least one pivot limitation, which limit the extension and/or flexion movement of the first pivot lever in its range of movement.

The adjustable orthesis joint according to the invention advantageously makes it possible to control the angles of the extension and flexion as well as the ulnar and radial deviation of the hand according to the state of health and therapy requirement of the patient. The angle of the or extension flexion may in this case advantageously be either fixed at 180° ($\gamma_1 = \gamma_2 = 0°$; outstretched hand) or enabled in a controlled way in various angle ranges of from 180° to 180°+$\gamma_1$ (dorsal extension), from 180° to 180°−$\gamma_2$ (palmar flexion) and in the entire range of movement of from 180°+$\gamma_1$ to 180°−$\gamma_2$, with $\gamma_1$, $\gamma_2$>0°. The angles $\delta_1$, $\gamma_2$ may for this purpose advantageously be adjusted by rotation of the upper and/or lower angle adjustment element to the respectively desired angle about the rotation axis.

An orthesis according to the invention having such an adjustable orthesis joint may therefore advantageously support the healing process in such a way that the freedom of movement t of the patient can be increased in a controlled way, movement permitted from a therapeutic point of view being guided in a controlled way and at the same time movements that are critical from a therapeutic point of view being fully or partially restrictable. In this way, unnecessary stiffness of healthy joints of the hand may advantageously be counteracted. The orthesis joint according to the invention in this case has a particularly compact and robust design, so that an orthesis according to the invention equipped therewith may likewise advantageously be configured compactly and hinders the patient little in their everyday life.

The dependent claims relate to further advantageous configurations and developments, which may be used individually or in combination with one another.

In one configuration of the invention, it has been found to be expedient that the at least one upper pivot limitation is arranged on a lower side of the first, upper angle adjustment element, the first, upper angle adjustment element preferably being configurable in the form of a disk. An upper pivot limitation arranged in such a way may advantageously be used to adjust the angle range of from $180°$ to $180°+\gamma_1$, i.e. to adjust the range of the dorsal extension.

In another preferred configuration, the first, upper, preferably disk-shaped angle adjustment element may comprise at least two, preferentially four upper pivot limitations arranged on the lower side, the pivot limitations being spaced apart from one another by an angle that is formed by the respective positions of the pivot limitations on the lower side and the point of intersection of the rotation axis with the lower side, and the pivot limitations being configured differently to one another in such a way that the extension movement of the first pivot lever is limited differently in its range of movement by cooperation with the various pivot limitations. Two or more upper pivot limitations arranged on the lower side, which are configured differently to one another and are arranged at an angle with respect to one another, advantageously make it possible to adjust various angle ranges of from $180°$ to $180°+\gamma_1$ for the dorsal extension, depending on the particular limitation angle $\gamma_1$ allowed by the pivot limitation respectively selected by rotation about the rotation axis.

Furthermore, a configuration of the invention has been found to be expedient in which the at least one lower pivot limitation is arranged on an upper side of the second, lower angle adjustment element, the second, lower angle adjustment element preferably being configurable in the form of a disk. A lower pivot limitation arranged in such a way may advantageously be used to adjust the angle range of from $180°$ to $180°-\gamma_2$, i.e. to adjust the range of the palmar flexion.

The second, lower, preferably disk-shaped angle adjustment element may in a further configuration also advantageously comprise at least two, preferentially four lower pivot limitations arranged on its upper side, the pivot limitations being spaced apart from one another by an angle that is formed by the respective positions of the pivot limitations on the upper side and the point of intersection of the rotation axis with the upper side; and the pivot limitations being configured differently to one another in such a way that the flexion movement of the first pivot lever is limited differently in its range of movement by cooperation with the various pivot limitations. Two or more lower pivot limitations arranged on the upper side, which are configured differently to one another and are arranged at an angle with respect to one another, advantageously make it possible to adjust various angle ranges of from $180°$ to $180°-\gamma_2$ for the palmar flexion, depending on the particular limitation angle $\gamma_2$ allowed by the pivot limitation respectively selected by rotation about the rotation axis.

Particularly preferentially, the pivot limitations may be configured as recesses in the first and/or second angle adjustment element, so that in the case of the first angle adjustment element, a thickness of the angle adjustment element is reduced from its lower side in the direction of its upper side in such a way that the first pivot lever is blocked after a swept angle $\gamma_1 \geq 0°$ during a pivot movement toward the first, upper angle adjustment element; and in the case of the second angle adjustment element, a thickness of the angle adjustment element is reduced from its upper side in the direction of its lower side in such a way that the first pivot lever is blocked after a swept angle $\gamma_2 0°$ during a pivot movement toward the second, lower angle adjustment element. Pivot limitations configured as recesses in the respective angle adjustment elements represent a particularly compact and at the same time robust solution for the angle limitation of the pivot movement of the first pivot lever, in which case additional components on the respective angle adjustment elements may advantageously be obviated.

In another preferred configuration of the invention, at least one upper latching means may be arranged on the lower side of the first, upper angle adjustment element, which is adapted to reversibly connect the upper angle adjustment element to the fastening element via at least one latching hole that is arranged on an upper side of the fastening element and is configured so as to correspond with the upper latching means, so that accidental rotation of the first angle adjustment element about the rotation axis is prevented.

As an alternative or in addition thereto, in one configuration of the invention, at least one lower latching means may be arranged on the upper side of the second, lower angle adjustment element, which is adapted to reversibly connect the lower angle adjustment element to the fastening element via at least one latching hole that is arranged on a lower side of the fastening element and is configured so as to correspond with the lower latching means, so that accidental rotation of the second angle adjustment element about the rotation axis is prevented.

Such lower and/or upper latching means having such correspondingly configured latching holes on the fastening element advantageously allow reversible fixing of the respective angle adjustment element, preferably independently of one another, on the fastening element in a position in which the respectively selected upper and/or lower pivot limitation can enter cleanly into active connection with the first pivot lever when a pivot movement is performed. Accidental twisting of the respective angle adjustment element about the rotation axis, which could disadvantageously lead to a deficient active connection when a pivot movement is being performed, is therefore advantageously prevented. If however, particularly in the case of two or more pivot limitations arranged on the respective angle adjustment elements, a respectively different pivot limitation is intended to be selected, the latching of the respective latching means may nevertheless be overcome by a relatively small but deliberate exertion of force and another pivot limitation may be brought into an active position.

Furthermore, a configuration of the present invention been found to be expedient in which at least one first stop and at least one second stop, which are adapted to limit the angle of the pivot movement of the second pivot lever, are arranged on the first pivot lever, the stops preferably being configured to be reversibly connectable to the first pivot lever. Such stops arranged on the first pivot lever advantageously also make it possible to limit the pivot movement of the second pivot lever about its articulation in order to perform an ulnar and radial deviation of the hand.

Lastly, a configuration of the present invention has been found to be expedient in which the second pivot lever comprises at least one slider which is adapted to movably connect the second pivot lever to a hand connecting element, the connecting element for this purpose preferably comprising a rail which is configured so as to correspond with said slider. Such a second pivot lever movably connected to a hand connecting element advantageously makes it possible, particularly in the case of a combined movement of the hand, for example in the case of a palmar flexion with a simultaneous ulnar or radial deviation, to accommodate the changing geometrical conditions (for example a variation of the optimal length conditions in respect of the distance of the articulation of the second pivot lever from a connecting point between the second pivot lever and the connecting element).

The present invention furthermore also relates to an orthesis for the controlled movement and/or fixation of a hand, or of a hand and a forearm, of a patient, having an adjustable orthesis joint as described above.

These as well as additional details and further advantages of the invention will be described below with the aid of preferred exemplary embodiments, although the present invention is not restricted thereto, and in connection with the appended drawing in which, schematically:

Figure 5:
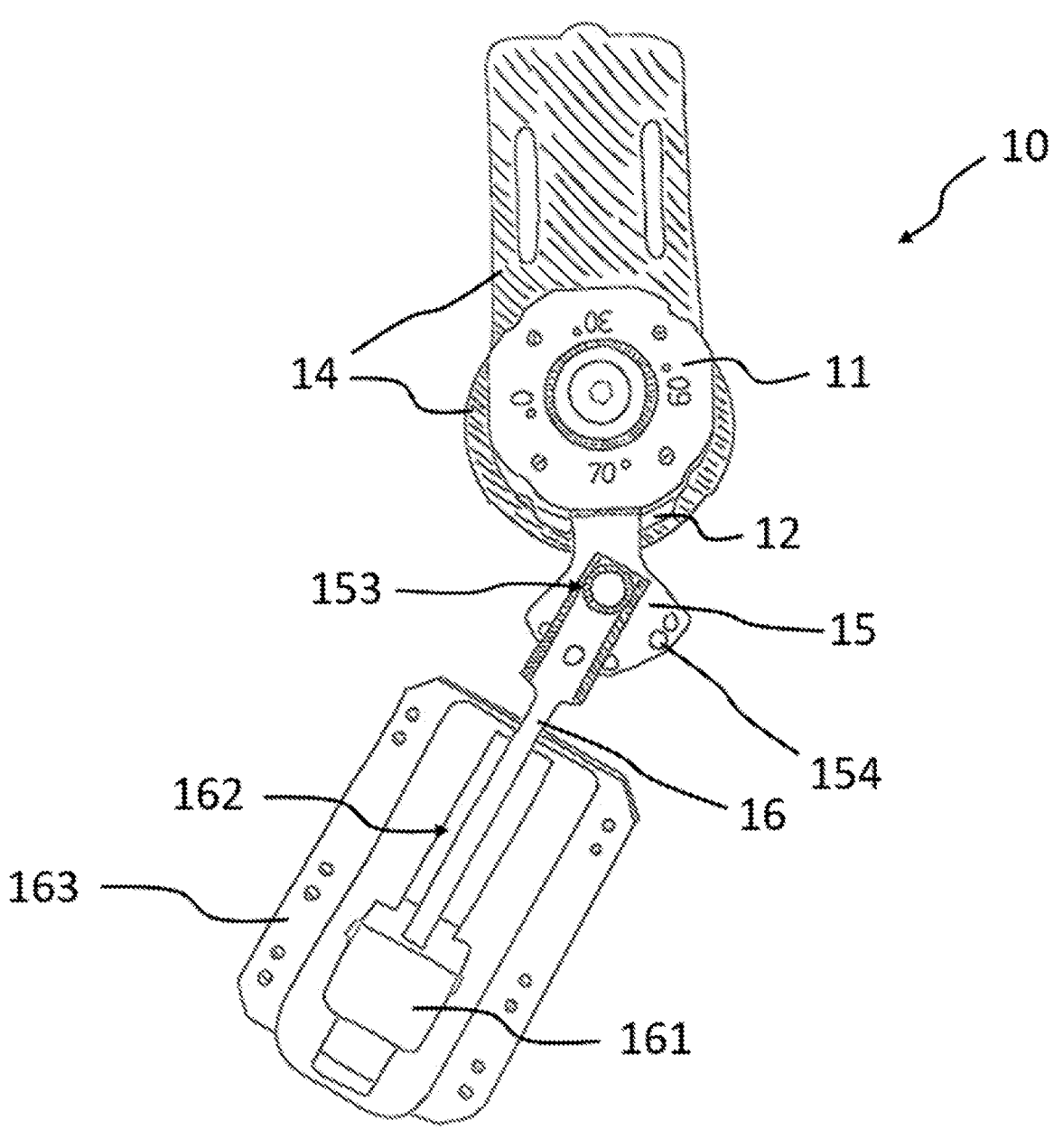
Figure 6:
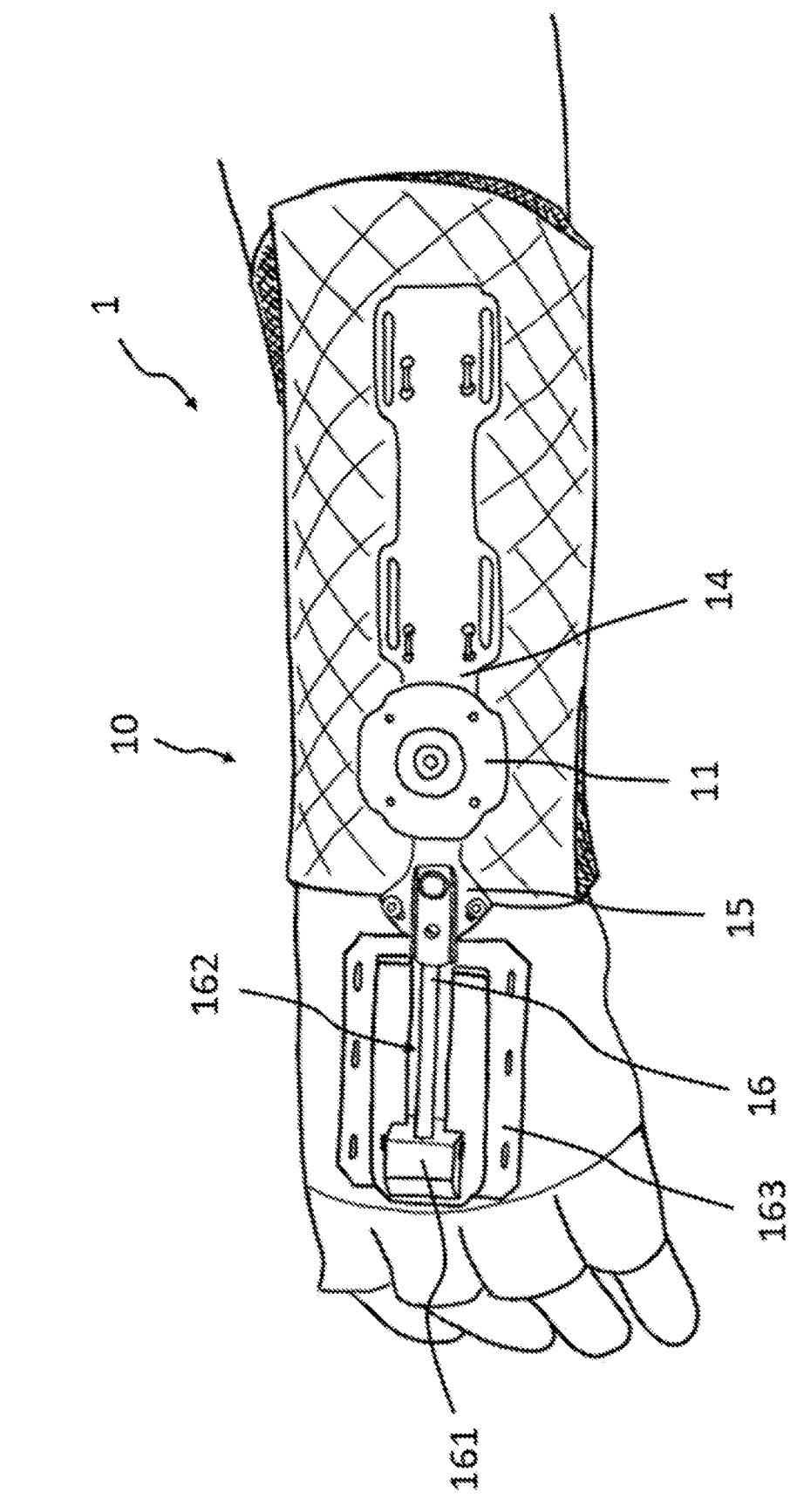

FIG. 5 above a further shows in a view from configuration of an orthesis joint according to the invention having a second pivot lever movably connected via a slider to a hand connecting element; and FIG. 6 shows in a view from above a configuration of an orthesis according to the invention during use.

In the following description of preferred embodiments of the present invention, the same reference signs denote component parts that are the same or similar.

Figure 1:
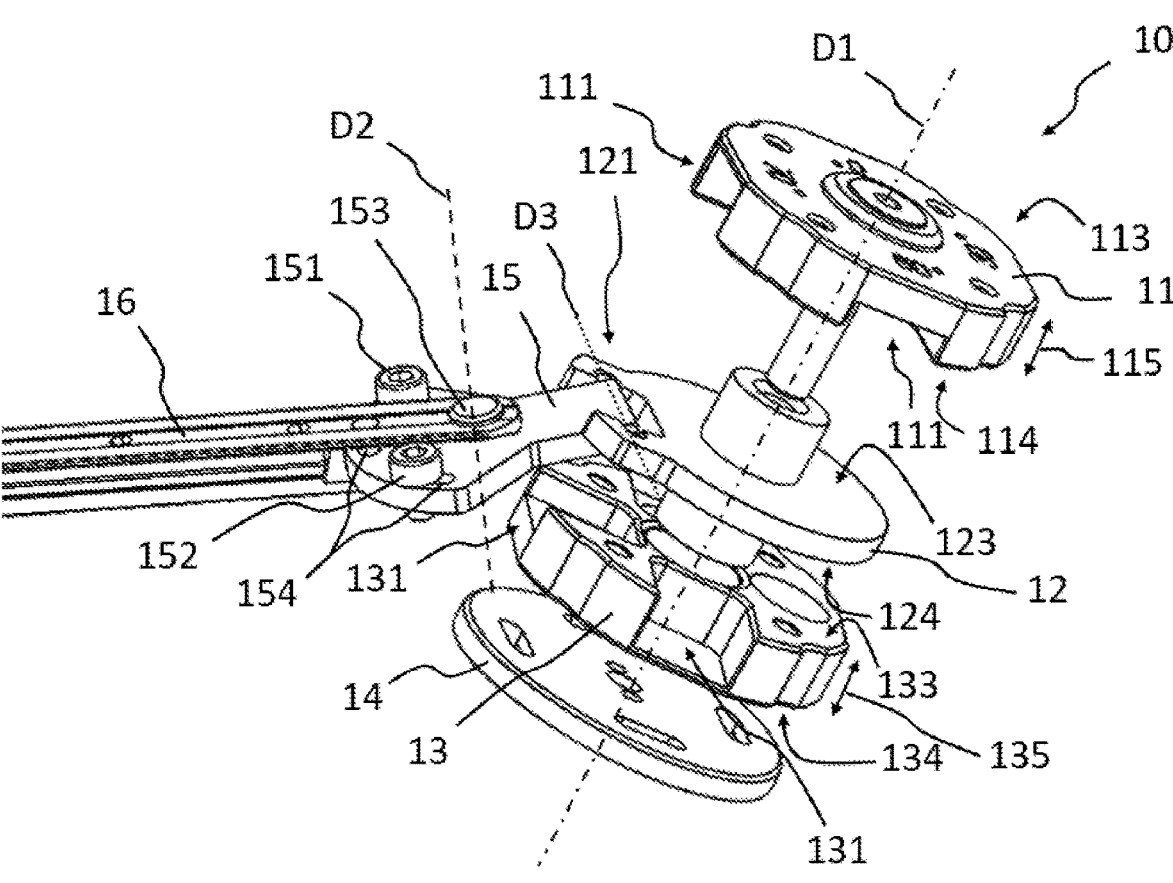
FIG. 1 shows a configuration of an orthesis joint according to the invention in a perspective exploded side view.

FIG. 1 shows a configuration of an orthesis joint 10 according to the invention in a perspective exploded side view.

An adjustable orthesis joint 10 according to the invention for the controlled movement and/or fixation of a hand of a patient comprises at least a first pivot lever 15 for performing an extension and/or flexion movement of the hand and a second pivot lever 16, arranged pivotably on the first pivot lever 15, for performing an ulnar and radial deviation of the hand. The orthesis joint 10 for this purpose comprises a preferably disk-shaped fastening element 12 on which the first pivot lever 15 is fastened, preferably via a pivot joint 121, and is configured to be pivotable about a rotation axis D3. The second pivot lever 16 may, in particular, be actively connected via an articulation 153 to the first pivot lever 15 and thereby be pivoted about a rotation axis D2, which is preferably aligned perpendicularly to the first pivot lever 15.

Figure 2:
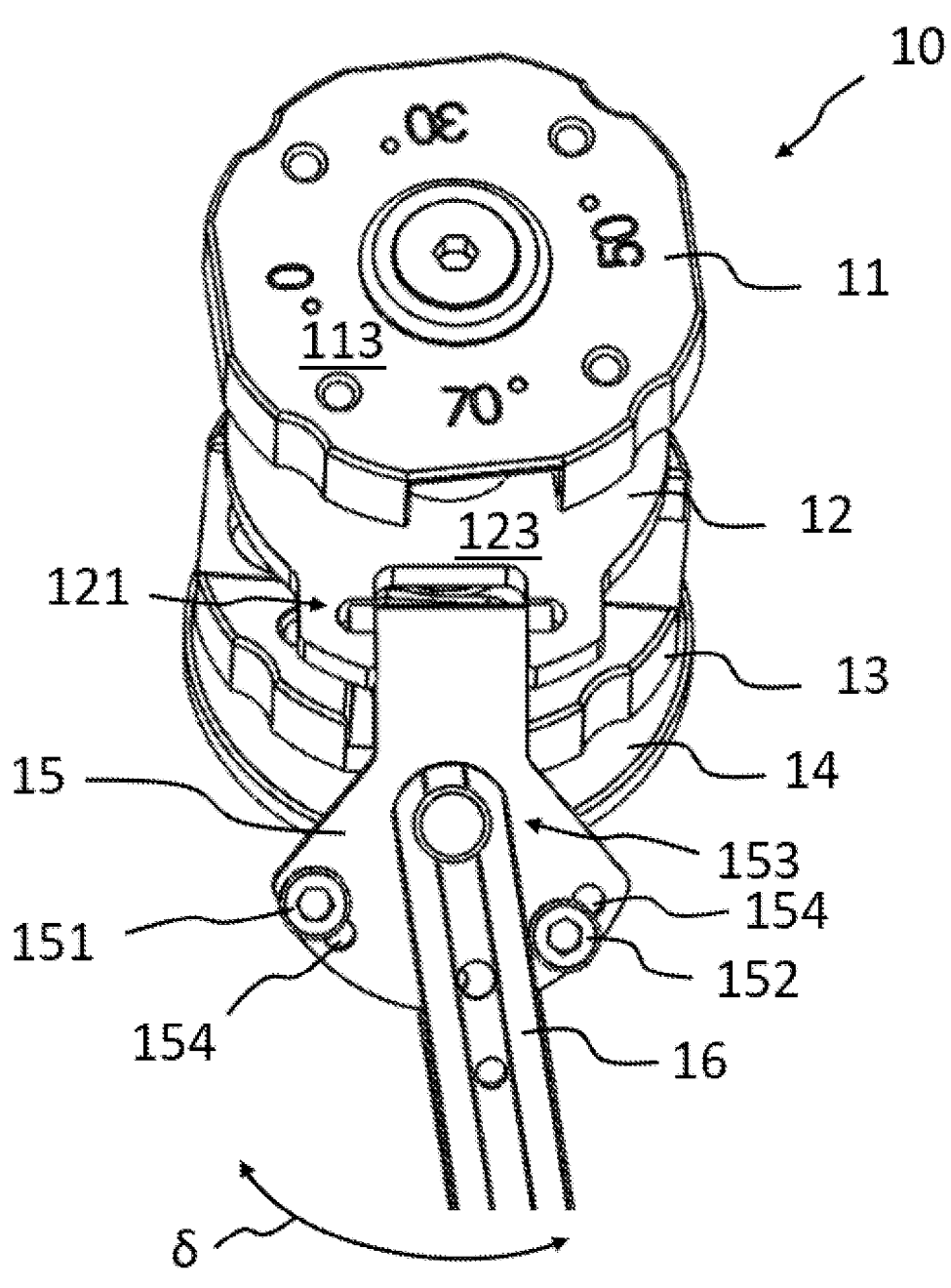
FIG. 2 shows the configuration of FIG. 1 in a perspective exploded view from above.

FIG. 2 shows the configuration of FIG. 1 in a perspective exploded view from above.

As may be seen here, the second pivot lever 16 may in this case preferably sweep a pivot angle δ, the pivot angle δ respectively lying on different planes of a sheaf of planes, the common line of which is specifically the rotation axis D3 of the first pivot lever 15, depending on the deflection of the first pivot lever 15. FIG. 2 also represents that at least one first stop 151 and at least one second stop 152, which are adapted to limit the angle δ of the pivot movement of the second pivot lever 16, may be arranged on the first pivot lever 15, the stops 151 and 152 preferably being configured to be reversibly connectable to the first pivot lever 15. The stops 151 and 152 may, in particular, be reversibly connectable to the first pivot lever 15 via fixing elements 154. For this purpose, FIG. 1 and FIG. 2 indicate fixing elements 154 which are configured as simple holes and through which the stops 15 and 152 can be simply inserted and screwed. Said fixing elements 154 configured as holes may in this case be elongated, as indicated in FIG. 1 and FIG. 2, although there may also be a plurality of holes placed close to one another, as shown in FIG.

4*b*. In particular magnetic holding locations, onto which the stops 151 and 152 may be reversibly placed, may however also be arranged as fixing elements 154 on the first pivot lever 15.

The orthesis joint 10 according to the invention furthermore comprises a first, upper, preferably disk-shaped angle adjustment element 11, which during use is arranged in relation to the back of a hand above the fastening element 12, rotatably about a rotation axis D1, on the fastening element 12, and a second, lower, preferably disk-shaped angle adjustment element 13, which during use is arranged in relation to the back of a hand below the fastening element 12, rotatably about the rotation axis D1, on the fastening element 12. The first angle adjustment element 11 and the second angle adjustment element 13 in this case each comprise at least one pivot limitation 111 or 131, which limit the extension and/or flexion movement of the first pivot lever 15 in its range of movement. The at least one upper pivot limitation 111 may, in particular, in this case be arranged on a lower side 114 of the first, upper, preferably disk-shaped angle adjustment element 11, and the at least one lower pivot limitation 131 may in particular be arranged on an upper side 133 of the second, lower, preferably disk-shaped angle adjustment element 13. In the present example, the first, upper angle adjustment element 11, the second, lower angle adjustment element 13 as well as the fastening element 12 are represented as approximately round disks, which have a similar diameter to one another and are arranged one above the other in a sandwich fashion, the individual planes being in other words arranged parallel to one another. The term "disk-shaped" in the context of the present invention is, however, also intended to mean components having contours that differ from a circle, and, in particular, the first, upper angle adjustment element 11 and the second, lower angle adjustment element 13 and/or the fastening element may also respectively have a polygonal contour, as also already indicated in FIG. 2. Furthermore, the first, upper angle adjustment element 11 may also be configured as a disk-shaped component having an approximately semicircular contour, which is arranged on the fastening element 12 perpendicularly to the plane of the latter (this is not represented here). The at least one upper pivot limitation 111 may in this case preferably be configured as the a stop which protrudes from the plane of perpendicularly arranged first, upper angle adjustment element 11 and can therefore limit, in particular, the dorsal extension movement of the first pivot lever 15 in its range of movement.

Preferred, however, is a configuration of an orthesis joint 10 according to the invention having at least two, particularly preferably—as represented in FIGS. 1 and 2—having four upper pivot limitations 111 arranged on the lower side 114 of the first, upper, preferably disk-shaped angle adjustment element 11, or having at least two, particularly preferably having four lower pivot limitations 131 arranged on the upper side 133 of the second, lower, preferably disk-shaped angle adjustment element 13. The number of pivot limitations 111 or 131 arranged on an angle adjustment element 11 or 13 is not, however, limited to the numbers two or four, but may vary and even be an odd number. The maximum number depends in principle only on the ratio of the selected width of the first pivot lever 15 in relation to the radius of the respective angle adjustment element 11 or 13. The narrower the first pivot lever 15 is, the more pivot limitations 111 or 131 configured so as to correspond therewith may be arranged on the angle adjustment elements 11 or 13 for the same radius of said respective angle adjustment elements 11 or 13.

If more than respectively one upper pivot limitation 111 and lower pivot limitation 131 are arranged on the angle adjustment elements 11 or 13, the upper pivot limitations 111 may be spaced apart from one another by an angle $\alpha$ that is formed by the respective positions of the pivot limitations 111 on the lower side 114 and the point of intersection of the rotation axis D1 with the lower side 114. Correspondingly, the lower pivot limitations 131 may be spaced apart from one another by an angle $\beta$ that is formed by the respective positions of the pivot limitations 131 on the upper side 133 and the point of intersection of the rotation axis D1 with the upper side 133 (cf. also FIG. 4 in this regard). In the example shown here, respectively having four pivot limitations 111 and 131 per angle adjustment element 11 and 13, the angles $\alpha$ and $\beta$ are both 90°. In the case of a suitably narrow first pivot lever 15, the number of pivot limitations 111 and 131 on the first, upper angle adjustment element 11 and on the second, lower angle adjustment element 13 may also be different to one another, and the angles $\alpha$ and $\beta$ may correspondingly be unequal.

FIG. 3 shows in partial figures a to d side views of details of a further configuration of an orthesis joint 10 according to the invention, which represent by way of example various movement angle ranges predefined by the respectively selected pivot limitations 111 and 131 on the respective angle adjustment element 11 and 13.

As represented in FIGS. 3a to d, the upper pivot limitations 111 or the lower pivot limitations 131 may preferentially be configured differently to one another in such a way that the extension or flexion movement of the first pivot lever 15 is limited differently in its range of movement by cooperation with the various upper 111 or lower 131 pivot limitations. The pivot limitations 111 or 131 may for this purpose particularly preferentially be configured as recesses in the first 11 and/or second 13 angle adjustment element, so that in the case of the first angle adjustment element 11, a thickness 115 of the angle adjustment element 11 is reduced from its lower side 114 in the direction of its upper side 113 in such a way that the first pivot lever 15 is blocked after a swept angle $\gamma_1 \geq 0°$ during a pivot movement toward the first, upper angle adjustment element 11; and in the case of the second angle adjustment element 13, a thickness 135 of the angle adjustment element 13 is reduced from its upper side 133 in the direction of its lower side 134 in such a way that the first pivot lever 15 is blocked after a swept angle $\gamma_2 \geq 0°$ during a pivot movement toward the second, lower angle adjustment element 13.

Figures 3A, 3B, 3C, 3D:
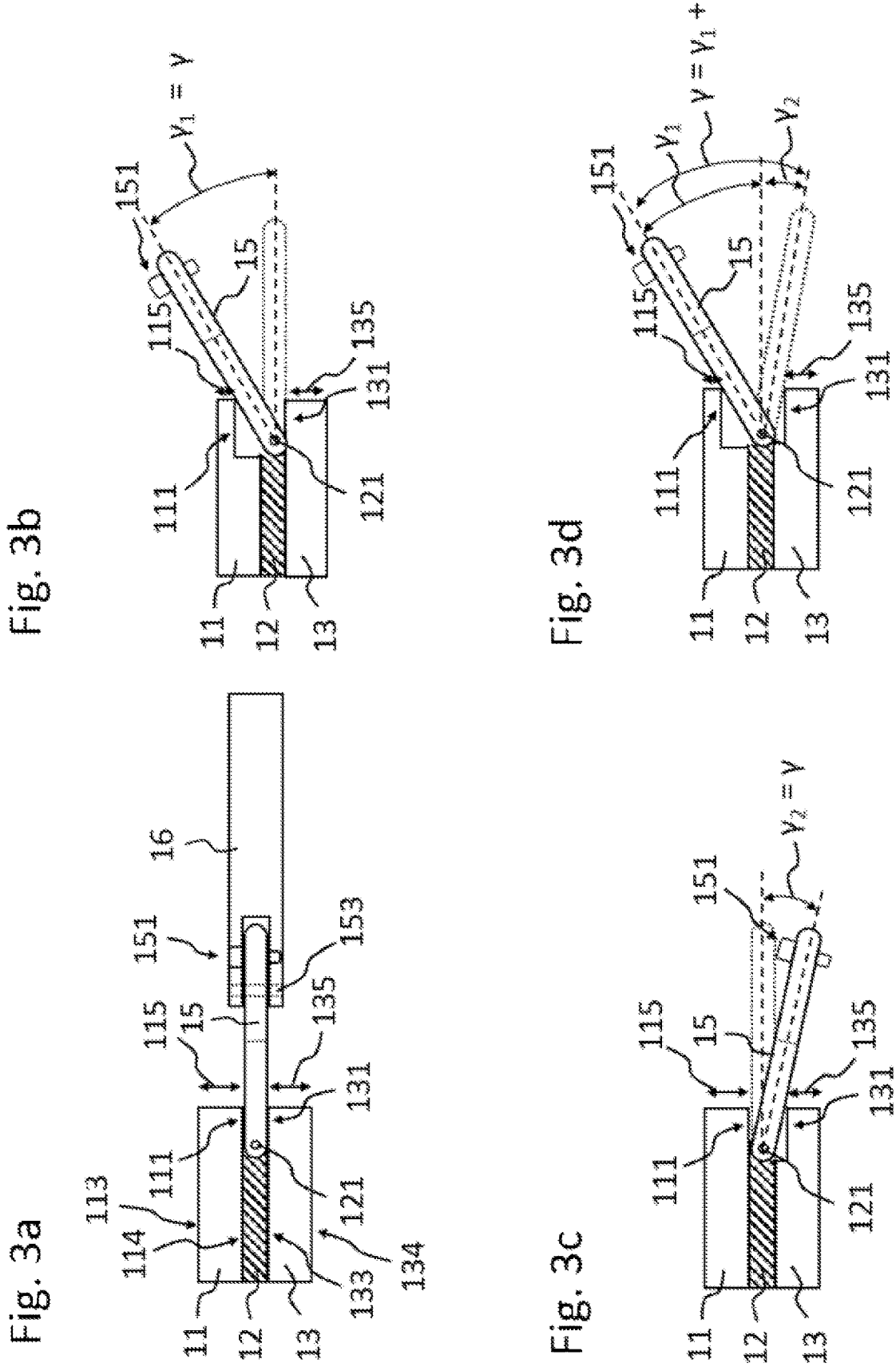
FIG. 3 shows in partial figures a to d side views of details of a further configuration of an orthesis joint according to the invention, which represent by way of example various movement angle ranges predefined by the respectively selected pivot limitations on the respective angle adjustment element.

FIG. 3a shows for example a setting of the orthesis joint 10 according to the invention in which the upper 111 as well as the lower 131 pivot limitations are configured identically, and do not reduce the thickness 115 of the first, upper angle adjustment element 11 and respectively the thickness 135 of the second, lower angle adjustment element 13. The angles $\gamma_1$ and $\gamma_2$ swept by the first pivot lever 15 are in this case equal to 0°—the extension or flexion movement of a hand that is supported by an orthesis having the orthesis joint 10 according to the invention would be fixed. The hand would be stretched out and could only perform an ulnar and radial deviation guided via the second pivot lever 16. In the subsequently described FIG. 3b to d, the second pivot lever 16 is not shown for the sake of clarity, but the functionality of the second pivot lever 16 remains as described above. FIG. 3b now shows a setting of the orthesis joint 10 according to the invention in which the upper pivot limitation 111 is configured as a recess, the thickness 115 of the angle adjustment element 11 being reduced from its lower side 114 in the direction of its upper side 113 in such a way that the first pivot lever 15 is blocked after a swept angle $\gamma_1 \geq 0°$ during a pivot movement toward the first, upper angle adjustment element 11. The lower pivot limitation 131 does not reduce the thickness 135 of the second, lower angle adjustment element 13 so that the angle $\gamma_2$ sweepable by the first pivot lever 15 is equal to 0°, as in FIG. 3a, since the lower pivot limitation 131 blocks any pivot movement of the first pivot lever 15. Such a setting of the orthesis joint 10 according to the invention, which may be achieved by simple rotation of the upper angle adjustment element 11 about the rotation axis D1 as far as a position of the first, upper angle adjustment element 11 in which the pivot limitation 111 configured suitably for the desired angle $\gamma_1$ can enter into active connection with the first pivot lever 15, allows for example only dorsal extension of the respective hand, in combination with which ulnar and radial deviation may again be performable. FIG. 3c correspondingly shows by way of example a setting of an orthesis joint 10 according to the invention in which the first, upper angle adjustment element 11, as in FIG. 3a, blocks any pivot movement of the first pivot lever 15 while the second, lower angle adjustment element 13 is in turn brought by rotation about the rotation axis D1 into a position in which the lower pivot limitation 131, entering into active connection with the first pivot lever 15 during a movement, is configured as recesses in the second angle adjustment element 13 and the thickness 135 of the angle adjustment element 13 is reduced from its upper side 133 in the direction of its lower side 134 in such a way that the first pivot lever 15 is blocked after a swept angle $\gamma_2 \geq 0°$ during a pivot movement toward the second, lower angle adjustment element 13. In the present example, the magnitude of the swept angle $\gamma_2$ is indicated as being less than that of the angle $\gamma_1$ in FIG. 3b. Said magnitudes could however also be equal, depending on which pivot limitations 111 or 131 are selected by the user. In FIG. 1 and FIG. 2, for this purpose the corresponding maximum movement angles are indicated in degrees—here 0°, 30°, 50° and 70°—on the upper side 113 of the first angle adjustment element 11, for example above each of the four upper pivot limitations 111 indicated here, although other angle specifications are naturally also possible. A corresponding marking may also be applied on the second, lower angle adjustment element 13 (this is not indicated here).

FIG. 3d lastly shows a setting of the orthesis joint 10 in which the two pivot limitations 111 and 131 allow pivot angles $\gamma_1$ and $\gamma_2$ greater than 0°. The possible total movement angle $\gamma$ of the first pivot angle 15 is in this case given by the sum of the two angles $\gamma_1$ and $\gamma_2$. In the example shown, said angles $\gamma_1$ and $\gamma_2$ are unequal, so that there is an asymmetrical maximum possible total movement; the two angles $\gamma_1$ and $\gamma_2$ could, however, also be equal (this is not represented), which would lead to a symmetrical maximum possible total movement.

Figures 4A, 4B, 4C:
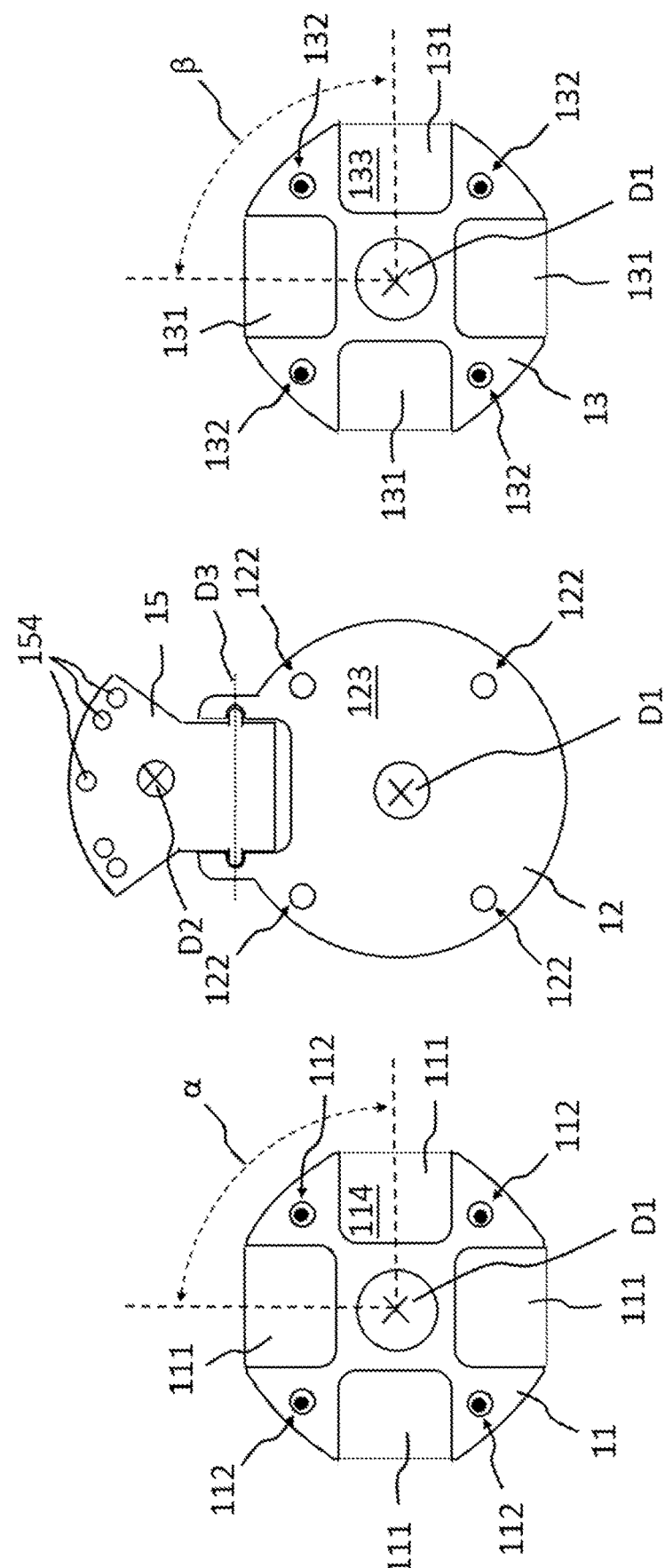
FIG. 4 shows in the partial drawings a to c a configuration of a first, upper angle adjustment element with a view of its lower side (FIG. 4*a*); a configuration of a fastening element with a view of its upper side (FIG. 4*b*) and a second, lower angle adjustment element with a view of its upper side (FIG. 4*c*)

FIG. 4 shows in the partial drawings a to c a configuration of a first, upper angle adjustment element 11 with a view of its lower side 114 (FIG. 4a); a configuration of a fastening element 12 with a view of its upper side 123 (FIG. 4b) and a second, lower angle adjustment element 13 with a view of its upper side 133 (FIG. 4c).

At least one upper latching means 112 may preferably be arranged on the lower side 114 of the first, upper angle adjustment element 11, which is adapted to reversibly connect the upper angle adjustment element 11 to the fastening element 12 via at least one latching hole 122 that is arranged on an upper side 123 of the fastening element 12 and is configured so as to correspond with the upper latching means 112, so that accidental rotation of the first angle adjustment element 11 about the rotation axis D1 is prevented. Correspondingly, as shown, at least one lower latching means 132 may be arranged on the upper side 133 of the second, lower angle adjustment element 13, which is adapted to reversibly connect the lower angle adjustment element 13 to the fastening element 12 via at least one latching hole 122 (not shown here) that is arranged on a lower side 124 of the fastening element 12 and is configured so as to correspond with the lower latching means 132, so that accidental rotation of the second angle adjustment element 13 about the rotation axis D1 is prevented.

The latching means 112 and 132—in FIGS. 4a and 4c four are shown by way of example on the upper 11 and respectively lower 13 angle adjustment element—may in particular be configured as small hollow grub screws, in which case the respective cavity of each grub screw may contain a spring that presses a ball outward at the open end of the grub screw. The respective ball surface then latches into the latching hole 122 which is intended therefor, and which is preferably configured as a groove, on the fastening element 12. Latching holes 122, in particular latching holes 122 configured as grooves, may for this purpose be arranged both on the upper side 123 and on the lower side 124 of the fastening element 12, as already mentioned. As an alternative or in addition thereto, the upper 112 and/or lower 132 latching means as well as the corresponding latching holes 122 may also be configured as simple milled portions (groove plus indentation, teeth, etc.). An advantage of the use of grub screws, as described above, is that the nature of the engagement or latching can thereby be defined accurately and at the same time it is an elegant but economical solution.

FIG. 5 shows in a view from above a further configuration of an orthesis joint 10 according to the invention having a second pivot lever 16 movably connected via a slider 161 to a hand connecting element 163.

In order to be fastened on an orthesis 1 for the controlled movement and/or fixation of a hand, or of a hand and a forearm, of a patient, the orthesis joint 10 according to the invention may also be terminated downward, i.e. toward the back of the hand or the forearm, by a cover plate 14, as shown in FIGS. 1, 2, 5 and 6. Said cover plate 14 may preferably be formed from any desired plastic; the first, upper 11 and second, lower 13 angle adjustment elements as well as the fastening element 12 may in particular be formed from aluminum, stainless steel or a medical plastic.

FIG. 5 also shows that the cover plate 14 may have an elongated shape which may extend in at least one direction beyond the extent of the first, upper 11 and/or second, lower 13 angle adjustment element, or beyond the fastening element 12. Such an elongated shape advantageously allows indirect or direct connection of the orthesis joint 10 via such a cover plate 14 to the forearm of a patient.

The second pivot lever 16 may furthermore comprise at least one slider 161 which is adapted to movably connect the second pivot lever 16 to a hand connecting element 163, for which purpose the connecting element 163 may preferably comprise a rail 162 which is configured so as to correspond with said slider 161. In FIG. 5, said connecting element 163 is represented as a plastic component. It may, however, also in turn be made from aluminum or stainless steel. Via the slider 161, in this configuration, the second pivot lever 16 is advantageously actively connected movably to the connecting element 163, the slider 161 as shown here preferably being capable of running in a correspondingly configured rail 162—here by way of example configured as a recess in the connecting element 163. When a combined movement of the hand is performed, for example a palmar flexion with simultaneous deviation or in the case of dorsal extension with simultaneous deviation, the connecting means 163 may therefore advantageously slide relative to the second pivot lever 16 and adapt to the geometrical conditions varying during a movement.

FIG. 6 lastly shows in a view from above a configuration of an orthesis 1 according to the invention during use.

The present invention relates to an adjustable orthesis joint 10 for the controlled movement and/or fixation of a hand of a patient and to an orthesis 1 having such an orthesis joint 10, which is distinguished in that it comprises at least one fastening element 12 for pivotable fastening of a first pivot lever 15; at least one first, upper angle adjustment element 11, and at least one second, lower angle adjustment element 13; the first angle adjustment element 11 and the second angle adjustment element 13 each comprising at least one pivot limitation 111 or 131, which limit the extension and/or flexion movement of a first pivot lever 15 in its range of movement. The adjustable orthesis joint 10 according to the invention advantageously makes it possible to control the angles of the extension and flexion as well as the ulnar and radial deviation of the hand according to the state of health and therapy requirement of the patient, while being advantageously compact and robust.

LIST OF REFERENCE SIGNS 1 orthesis
10 orthesis joint
11 first, upper angle adjustment element
    111 upper pivot limitation
    112 upper latching means
    113 upper side of the first angle adjustment element (11)
    114 lower side of the first angle adjustment element (11)
    115 thickness of the first, upper angle adjustment element (11)
12 fastening element
    121 pivot joint for first pivot lever (15)
    122 latching hole
    123 upper side of the fastening element (12)
    124 lower side of the fastening element (12)
13 second, lower angle adjustment element
    131 lower pivot limitation
    132 lower latching means
    133 upper side of the second angle adjustment element (13)
    134 lower side of the second angle adjustment element (13)

135 thickness of the second, lower angle adjustment element (13)
14 cover plate
15 first pivot lever for extension/flexion (E/F)
   151 first stop
   152 second stop
   153 articulation for the second pivot lever (16)
   154 fixing element for stops (151; 152)
16 second pivot lever for ulnar/radial deviation (urD) of the hand
   161 slider
   162 rail
   163 hand connecting element
$\alpha$ angle between the upper pivot limitations (111)
$\beta$ angle between the lower pivot limitations (131)
$\gamma$ total movement angle of the first pivot lever (15); $\gamma = \gamma_1 + \gamma_2$
$\gamma_1$ angle of the pivot movement of the first pivot lever (15) toward the first, upper angle adjustment element (11)
$\gamma_2$ angle of the pivot movement of the first pivot lever (15) toward the second, lower angle adjustment element (13)
$\delta$ angle of the pivot movement of the second pivot lever (16)
D1 rotation axis of the angle adjustment elements (11; 13)
D2 rotation axis of the articulation (153) for the second pivot lever (16)
D3 rotation axis of the pivot joint (121) for the first pivot lever (15)

The invention claimed is:

1. An adjustable orthesis joint (10) for the controlled movement and/or fixation of a hand of a patient, comprising at least
   a first pivot lever (15) for performing an extension and/or flexion movement of the hand;
   a second pivot lever (16), arranged pivotably on the first pivot lever (15), for performing an ulnar and/or radial deviation of the hand;
wherein
   the orthesis joint (10) comprises
     a fastening element (12) for pivotable fastening of the first pivot lever (15);
     a first, upper angle adjustment element (11), which during use is arranged in relation to the back of a hand above the fastening element (12), rotatably about a rotation axis (D1), on the fastening element (12); and
     a second, lower angle adjustment element (13), which during use is arranged in relation to the back of a hand below the fastening element (12), rotatably about the rotation axis (D1), on the fastening element (12);
     the first angle adjustment element (11) and the second angle adjustment element (13) each comprising at least one pivot limitation (111; 131), which limit the extension and/or flexion movement of the first pivot lever (15) in a range of movement.

2. The orthesis joint (10) of claim 1, wherein
the first, upper angle adjustment element (11) comprises at least two upper pivot limitations (111) arranged on the lower side (114),
the pivot limitations (111) being spaced apart from one another by an angle (a) that is formed by the respective positions of the pivot limitations (111) on the lower side (114) and the point of intersection of the rotation axis (D1) with the lower side (114);
and the pivot limitations (111) being configured differently to one another in such a way that the extension movement of the first pivot lever (15) is limited differently in its range of movement by cooperation with the various pivot limitations (111).

3. The orthesis joint (10) of claim 2, wherein the first, upper angle adjustment element (11) comprises four upper pivot limitations (111) arranged on the lower side (114).

4. The orthesis joint (10) of claim 1, wherein
the second, lower angle adjustment element (13) comprises at least two lower pivot limitations (131) arranged on the upper side (133),
the pivot limitations (131) being spaced apart from one another by an angle ($\beta$) that is formed by the respective positions of the pivot limitations (131) on the upper side (133) and the point of intersection of the rotation axis (D1) with the upper side (133);
and
the pivot limitations (131) being configured differently to one another in such a way that the flexion movement of the first pivot lever (15) is limited differently in its range of movement by cooperation with the various pivot limitations (131).

5. The orthesis joint (10) of claim 4, wherein the second, lower angle adjustment element (13) comprises four lower pivot limitations (131) arranged on the upper side (133).

6. The orthesis joint (10) of claim 1, wherein at least one first stop (151) and at least one second stop (152), which are adapted to limit an angle ($\delta$) of the pivot movement of the second pivot lever (16), are arranged on the first pivot lever (15).

7. The orthesis joint (10) of claim 6, wherein the stops (151; 152) are configured to be reversibly connectable to the first pivot lever (15).

8. The orthesis joint (10) of claim 1, wherein the second pivot lever (16) comprises at least one slider (161) which is adapted to movably connect the second pivot lever (16) to a hand connecting element (163).

9. The orthesis joint (10) of claim 8, wherein the hand connecting element (163) comprises a rail (162) which is configured so as to correspond with the slider (161) of the second pivot lever (16).

10. The orthesis joint (10) of claim 1, wherein the at least one upper pivot limitation (111) is arranged on a lower side (114) of the first, upper angle adjustment element (11).

11. The orthesis joint (10) of claim 1, wherein the at least one lower pivot limitation (131) is arranged on an upper side (133) of the second, lower angle adjustment element (13).

12. The orthesis joint (10) of claim 1, wherein the pivot limitations (111; 131) are configured as recesses in the first (11) and/or second (13) angle adjustment element, so that
   in the case of the first angle adjustment element (11), a thickness (115) of the angle adjustment element (11) is reduced from its lower side (114) in the direction of its upper side (113) in such a way that the first pivot lever (15) is blocked after a swept angle $\gamma 1 \geq 0°$ during a pivot movement toward the first, upper angle adjustment element (11); and
   in the case of the second angle adjustment element (13), a thickness (135) of the angle adjustment element (13) is reduced from its upper side (133) in the direction of its lower side (134) in such a way that the first pivot lever (15) is blocked after a swept angle $\gamma 2 \geq 0°$ during a pivot movement toward the second, lower angle adjustment element (13).

13. The orthesis joint (10) of claim 1, wherein at least one upper latching means (112) is arranged on the lower side (114) of the first, upper angle adjustment element (11), which is adapted to reversibly connect the upper angle adjustment element (11) to the fastening element (12) via at least one latching hole (122) that is arranged on an upper side (123) of the fastening element (12) and is configured so as to correspond with the upper latching means (112), so that accidental rotation of the first angle adjustment element (11) about the rotation axis (D1) is prevented;

and/or in that at least one lower latching means (132) is arranged on the upper side (133) of the second, lower angle adjustment element (13), which is adapted to reversibly connect the lower angle adjustment element (13) to the fastening element (12) via at least one latching hole (122) that is arranged on a lower side (124) of the fastening element (12) and is configured so as to correspond with the lower latching means (132), so that accidental rotation of the second angle adjustment element (13) about the rotation axis (D1) is prevented.

14. An orthesis (1) for the controlled movement and/or fixation of a hand, or of a hand and a forearm, of a patient, comprising the adjustable orthesis joint (10) of claim 1.

15. The orthesis joint (10) of claim 1, wherein the first, upper angle adjustment element (11) is configured in form of a disk.

16. The orthesis joint (10) of claim 1, wherein the second, lower angle adjustment element (13) is configured in the form of a disk.

\* \* \* \* \*